United States Patent
Yang et al.

(10) Patent No.: US 6,326,509 B1
(45) Date of Patent: Dec. 4, 2001

(54) PROCESS FOR AZOLE ANTIFUNGAL INTERMEDIATE

(75) Inventors: Wangying Yang, Plainsboro; Xuebao Wang, East Brunswick, both of NJ (US); Apurba Bhattacharya, Corpus Christi, TX (US); Melissa Chau, Brooklyn, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/568,874

(22) Filed: May 9, 2000

Related U.S. Application Data

(60) Provisional application No. 60/135,054, filed on May 20, 1999.

(51) Int. Cl.$^7$ .................................................. C07C 69/76
(52) U.S. Cl. ................................................................ 560/8
(58) Field of Search ..................................... 560/8

(56) References Cited

U.S. PATENT DOCUMENTS 5,648,372    7/1997    Naito et al. .

FOREIGN PATENT DOCUMENTS

WO 99/61017    5/1999    (WO) .

OTHER PUBLICATIONS

CA 53:4119f: B.F. Pishnamazzade et al, "The Alkylation of Chloromethyl Esters of Carboxylic Acids with Olefins", Doklady Akd. Nauk Azer. S.S.R., vol. 12 (1956) pp. 895–900.*
Manoucherhr Saljoughain et al, "A New and Efficient Synthesis of Monotritiomethyl Iodide", J. Labelled Cmpds. and Radiopharm. vol. 27(7) (1989), pp. 767–776.*
CA 131:258769: Zhong Shen et al, "Chloromethylation and Hydroxymethylation of SEBS", Gaodeng Xuexiao Huaxue Xuebao, vol. 20(5), (1999), pp. 827–829.*
L.H. Ulich et al, "The Reaction Between Acid Halides and Aldehydes. III", J. Amer. Chem. Soc., vol. 43 (1921), pp. 660–667.*
Lysenko, Y., et al, "Electrolytic Dissociation of Complexes in Systems Formed by Tin Tetrachloride and Esters of Halo Alcohols," Chem. Abstr., Abstract No. 49129, vol. 73, Zh. Obshch. Khim. 40(4), pp. 737–739, 1970.
R P. Iyer, et al, "Synthesis of Iodoalkylacylates and Their Use in the Preparation of S–Alkyl Phosphorothiolates," Synthetic Communications, 25(18), pp. 2739–2749, 1995.

* cited by examiner

Primary Examiner—Gary Geist
Assistant Examiner—M. P. Moon
(74) Attorney, Agent, or Firm—David M. Morse

(57) ABSTRACT

An improved process is provided for synthesis of a halomethyl benzoic acid chloromethyl ester, a key intermediate for use in production of azole antifungal compounds and other pharmaceutical products.

1 Claim, No Drawings

PROCESS FOR AZOLE ANTIFUNGAL INTERMEDIATE

CROSS-REFERENCE TO RELATED APPLICATIONS

This application claims the benefit of U.S. Provisional Patent Application Ser. No. 60/135,054 filed May 20, 1999.

BACKGROUND OF THE INVENTION

This invention relates to an improved process for preparing a key intermediate useful in the synthesis of triazole antifungal compounds and other pharmaceutical compounds. In particular, the present invention provides an improved process for preparing a halomethyl benzoic acid chloromethyl ester which can be used, for example, to prepare triazole antifungal agents such as those described by our colleagues in co-pending U.S. Pat. No. 60/103,560 filed Oct. 7, 1998 and U.S. Pat. No. 6,265,584 issued Jul. 24, 2001, all of which applications being hereby incorporated by reference.

The intermediate, halomethyl benzoic acid chloromethyl ester, having the general formula

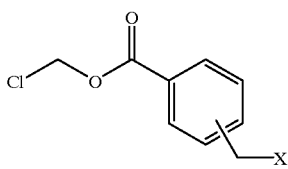

I wherein X is Cl, Br or I and the halomethyl substituent is in the ortho, meta or para position of the phenyl ring is reported in the above-identified applications as being made by reacting the acid chloride of the formula

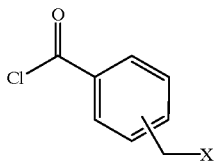

wherein X is as defined above with paraformaldehyde and zinc chloride in benzene. This method is also described by Iyer et. al. in Syn. Comm., 25, 2739, 1995. It suffers from several disadvantages, e.g. it is necessary to use benzene as the solvent and it requires a chromatography step.

The present inventors have discovered that the same acid chloride of the formula

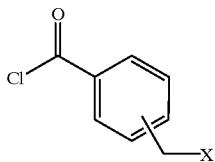

wherein X is Cl, Br or I and the halomethyl substituent is in the ortho, meta or para position of the phenyl ring can be reacted with SnCl$_4$ and 1,3,5-trioxane in an inert organic solvent such as methylene chloride to give key intermediate I in improved yields without many of the disadvantages of the above-mentioned process. For example, it is no longer necessary to use benzene as the solvent and the chromatography step is eliminated.

Intermediate I may be used to produce a number of biologically active products as illustrated below by its conversion to triazole antifungal agents.

SUMMARY OF THE INVENTION

The present invention provides a process for preparing the intermediate of the formula

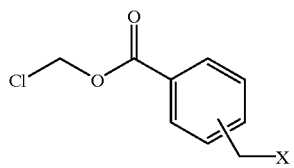

I wherein X is Cl, Br or I and the halomethyl substituent is in the ortho, meta or para position of the phenyl ring, which comprises reacting an acid chloride of the formula

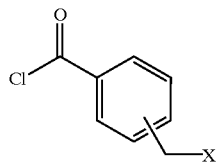

wherein X is as defined above and the halomethyl substituent is in the ortho, meta or para position of the phenyl ring with SnCl$_4$ and 1,3,5-trioxane in an inert organic solvent.

Intermediate I can be employed in the production of pharmaceutical compounds such as azole antifungal agents of the general formula

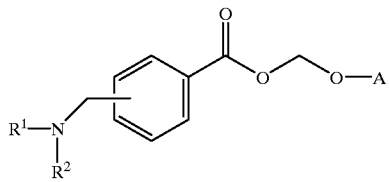

wherein A is the non-hydroxy portion of a triazole antifungal compound of the type containing a secondary or tertiary hydroxy group and $R^1$ and $R^2$ are hydrogen, $C_1$–$C_6$ alkyl or $C_2$–$C_6$ alkyl, said alkyl or alkenyl group being optionally substituted by a hydroxy or dimethylamino group, or $R^1$ and $R^2$ taken together with the nitrogen to which they are attached form a heterocyclic group of the formula

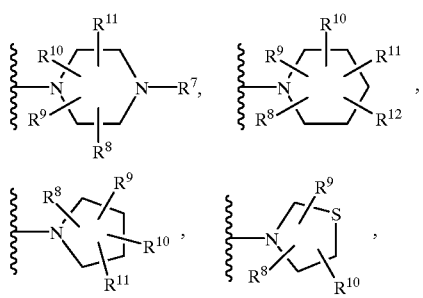

-continued

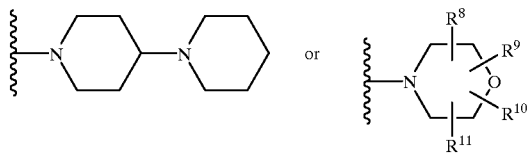

where $R^7$ is hydrogen, CHO, $COR^{13}$ or $C_1-C_6$ alkyl in which the alkyl group may be optionally interrupted by an oxygen atom or $NR^{14}$ and may be substituted by hydroxy, $R^8$, $R^9$, $R^{10}$, $R^{11}$ and $R^{12}$ are each independently hydrogen, hydroxy, $CONH_2$, or $C_1-C_6$ alkyl, said alkyl group being optionally substituted by hydroxy, $R^{13}$ is $C_1-C_6$ alkyl and $R^{14}$ is hydrogen or $C_1-C_6$ alkyl; or a pharmaceutically acceptable salt thereof.

A preferred triazole antifungal parent compound for use in preparing the above-mentioned prodrugs is (2R,3R)-3-[4-(4-cyanophenyl)thiazol-2-yl]-2-(2,4-difluorophenyl)-1-(1H-1,2,4-triazol-1-yl)-butan-2-ol described in U.S. Pat. No. 5,648,372 and having the formula

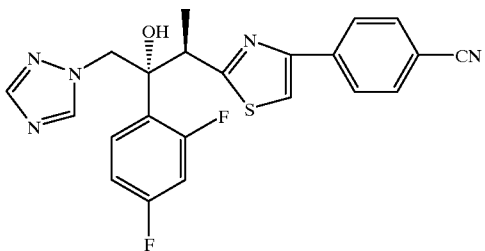

DESCRIPTION OF THE PREFERRED EMBODIMENTS

The process of the present invention comprises reacting halomethylbenzoyl chloride with $SnCl_4$ and 1,3,5-trioxane in an inert organic solvent such as methylene chloride. The reaction may be carried out at room temperature and the co-produced dimeric impurity, methanediol bis halomethylbenzoate, may be removed by slurrification in heptane containing ethyl acetate. Upon distillative removal of ethyl acetate, the desired intermediate product may be directly crystallized from heptane.

Example 1 below describes in more detail a preferred embodiment for carrying out the present invention.

Example 2 below describes use of intermediate I to produce a biologically active azole antifungal agent.

The end-products such as (2R,3R)-3-[4-(4-cyanophenyl) thiazol-2-yl]-2-(2,4-difluorophenyl)-1-(1H-1,2,4-triazol-1-yl)-2-[[m-(N,N-dimethylaminomethyl)-benzoyloxy] methoxy]butane prepared in Example 2 below act as prodrugs of the parent azole antifungal agents when administered in vivo to mammals.

The pharmaceutically active compounds prepared using the intermediate of the present invention, such as Example 2 below, may be used alone or formulated as pharmaceutical compositions comprising, in addition to the active triazole ingredient, a pharmaceutically acceptable carrier, adjuvant or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Alternatively, the bioactive azole compounds prepared using the intermediate of the present invention can be administered in the form of a suppository or pessary, or they may be applied topically in the form of a lotion, solution, or cream. Additionally, they may be incorporated (at a concentration up to 10%) into an ointment consisting of a white wax or soft, white paraffin base together with the required stabilizers and/or preservatives.

The bioactive azole end-products are useful because they possess pharmacological activities in animals, including particularly mammals and most particularly, humans. Specifically, the azole end-products are useful for the treatment or prevention of topical fungal infections, including those caused by species of Candida, Trichophyton, Microsporum, or Epidermophyton. Additionally, they are useful for the treatment of mucosal infections caused by Candida albicans. They can also be used in the treatment of systemic fungal infections caused, for example, by species of Candida albicans, Cryptococcus neoformans, Aspergillus flavus, Aspergillus fumigatus, Coccidioides, Paracoccidiodes, Histoplasma, or Blastomyces.

The dosage to be administered for the bioactive azole end-products depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 5 mg/day to about 1.0 g/day. These doses are exemplary of the average case, and there can be individual instances where higher or lower dosages are merited. Furthermore, administration of the compounds can be conducted in either single or divided doses.

The in vitro evaluation of the antifungal activities of the bioactive azole compounds can be performed by determining the minimum inhibitory concentration (MIC). The MIC is the concentration of test compound which inhibits the growth of the test microorganism. In practice, a series of agar plates, each having the test compound incorporated at a specific concentration, is inoculated with a fungal strain and each plate is then incubated for 48 h at 37° C. The plates are examined for the presence or absence of fungal growth, and the relevant concentration is noted. Microorganisms which can be used in the test include Candida albicans, Asperigillus fumigatus, Trichophyton spp., Microsporum spp., Epidermophyton floccosum, Coccidioides immitis, and Torulopsos galbrata. It should be recognized that, as prodrugs, some compounds prepared from the intermediates of the present invention may not be active in the in vitro test.

The in vivo evaluation of bioactive azole end-products such as the compound of Example 2 can be carried out at a series of dose levels by intraperitoneal or intravenous injection or by oral administration to mice which have been inoculated with a strain of fungus (e.g. *Candida albicans*). Activity is determined by comparing the survival of the treated group of mice at different dosage levels after the death of an untreated group of mice. The dose level at which the test compound provides 50% protection against the lethal effect of the infection is noted.

The azole end-products substantially increase the solubility of the parent triazole antifungal compound and also release the bioactive parent compound (i.e. function as a prodrug) in both rat and human plasma.

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | |
|---|---|
| h = | hour(s) |
| rt = | room temperature |
| mol = | mole(s) |
| mmol = | mmole(s) |
| g = | gram(s) |
| THF = | tetrahydrofuran |
| L = | liter(s) |
| mL = | milliliter(s) |
| Et$_2$O = | diethyl ether |
| EtOAc = | ethyl acetate |
| MeOH = | methanol |
| DMF = | dimethylformamide |
| DABCO = | 1,4-Diazabicyclo[2.2.]octane |

In the following examples, all temperatures are given in degrees Centigrade. Melting points were determined on an electrothermal apparatus and are not corrected. Proton nuclear magnetic resonance ($^1$H NMR) spectra were recorded on a Bruker AM-300 or a Varian Gemini 300 spectrometer. All spectra were determined in CDCl$_3$, DMSO-d$_6$, CD$_3$OD, or D$_2$O unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50 or a Finnegan 4500 instrument utilizing direct chemical ionization (DCI, isobutene), fast atom bombardment (FAB), or electron ion spray (ESI).

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure.

EXAMPLE 1

Preparation of (3-Chloromethyl)Benzoic Acid Chloromethyl Ester

A. Prior Art Method

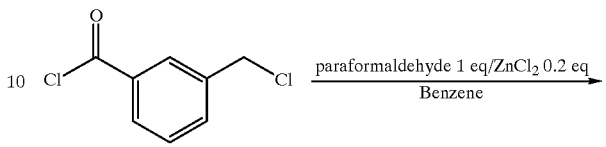

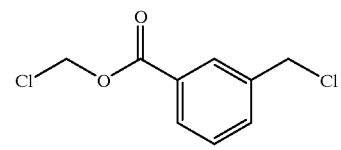

To a cooled (0° C.) mixture of paraformaldehyde (0.79 g, 26.4 mmol) and zinc chloride (72 mg, 0.53 mmol) in benzene (10 mL) was added dropwise the acid chloride (5.0 g, 26.4 mmol) over a period of 15 minutes. The mixture was then heated at 55° C. overnight. The mixture was then filtered and the filtrate concentrated. Purification of the crude product via flash chromatography (100% Hexanes) yielded 2.7 g of the title compound as a colorless oil.

B. Method of Present Invention

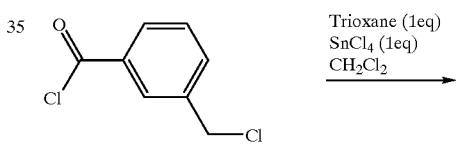

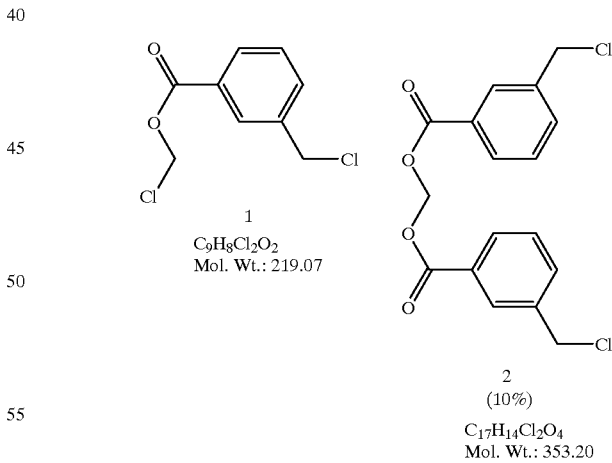

1
C$_9$H$_8$Cl$_2$O$_2$
Mol. Wt.: 219.07

2
(10%)
C$_{17}$H$_{14}$Cl$_2$O$_4$
Mol. Wt.: 353.20

MATERIALS

3-Chloromethylbenzoyl chloride: 30 g (0.159 mole, 22.6 mL, Aldrich)
Tin (IV) Chloride: (41.35 g, 18.57 mL, 158 mole, Aldrich)
1,3,5-trioxane (14.29 g of 99% purity, 0.158 mole, Aldrich)
Dichloromethane (120 mL, EM Science, HPLC grade, KF=0.2 mG/mL)

Heptane (470 mL, EM Science, HPLC grade)
Ethylacetate (4.5 mL, EM Science, HPLC grade)
Aq. NaHCO$_3$ solution (saturated); 100 ml
Water (Deionised, 220 mL)

PROCEDURE

A 500 ml three neck round bottom flash equipped with a nitrogen inlet, reflux condenser, addition funnel, mechanical stirrer and immersion thermometer was charged with 60 mL CH$_2$Cl$_2$ (KF=0.2 mg/mL) and 3-chloromethylbenzoylchloride. Tin (IV) chloride was added via the addition funnel with stirring over a period of 2 minutes maintaining a temperature of 20° C.–22° C. 1,3,5-trioxane was added to the stirred mixture. The majority of the 1,3,5-trioxane remains undissolved.

The stirred suspension was kept at 20° C.–22° C. for 24 hours at the end of which the conversion was 99% (L.C. area percent). Approximately 10% of the dimer (2) was also observed by HPLC.

The reaction mixture was quenched by the addition of 120 mL water via the addition funnel maintaining the internal temperature between 15° C.–20° C.

The reaction mixture (containing some suspended solid particles) was filtered through a sintered glass funnel (polish filtration) and the solids were washed with 120 mL CH$_2$Cl$_2$. After settling, the two layers clearly separated.

The lower CH$_2$Cl$_2$ layer containing the product was separated from the top aqueous layer. The organic layer was washed with 100 mL water and the lower CH$_2$Cl$_2$ layer containing the product was separated from the top aqueous layer.

The lower CH$_2$Cl$_2$ layer containing the product was separated from the top aqueous layer. The organic layer was washed with 100 mL saturated aq. NaHCO$_3$ solution and the lower CH$_2$Cl$_2$ layer containing the product was separated from the top aqueous layer.

The lower CH$_2$Cl$_2$ layer containing the product was separated from the top aqueous layer. The CH$_2$Cl$_2$ was then replaced by heptane via distillation (under atmospheric pressure) maintaining a total volume of approximately 450 mL.

Distillation was discontinued when the batch temperature reached approximately 80° C. NMR analysis of the mixture indicated complete removal of CH$_2$Cl$_2$ at this point. Approximately 470 mL heptane was used.

The mixture was cooled down to 22° C. Ethylacetate (4.5 mL) was added to the stirred mixture and the stirred mixture was kept at 22° C for 18 h. The less soluble methanediol bis (3-chloromethyl)benzoate (2) is crystallized out in this process. Addition of ethylacetate helps to keep the desired product (1) in solution. When the heptane solution is cooled down to approximately 30–40° C., some crystallization of the dimer was observed and a seed bed is formed. If the dimer does not crystallize by cooling down to 22° C., additional cooling to 0–5° C. may be necessary for the seed bed to be formed.

The crystals (dimer 2) were filtered and washed with 60 mL heptane. Approximately 4.4 gm of the dimer, methanediol bis (3-chloromethyl)benzoate was obtained.

The combined filtrate and wash containing the product was concentrated via distillation under house vacuum to approximately 100 mL volume. The mixture was cooled to 22° C. over a period of one hour with seeding (at 35° C.). Crystallization begins at approximately 30° C. to 35° C. Since the compound melts at 42° C., the mixture should not be seeded above 40° C.

The stirred mixture was cooled to 0–5° C. over a period of 30 minutes and then kept at 0–5° C. for 2 hours. The crystals were filtered, washed with 20 mL of cold (10° C.) heptane, and dried in a vacuum oven at 20–22° C. with a flow of nitrogen for 18 hours to yield 25.8 g (74% yield).

ANALYSES

M.P.=41–42° C. NMR=consistent with the structure.
HPLC

| Instrument: | Shimadzu LC-10AS |
| --- | --- |
| HPLC Detector: | Shimadzu SPD M10A Diode Array (260 nm) |
| Column: | YMC ODS AQ 4.6 × 150 mm, S-3 µm, 120A |
| Injection vol: | 10 µL |
| Flow Rate: | 1.5 mL/min |
| Run Time: | 25 min |
| Eluent A: | CH$_3$CN/water 10:90 |
| Eluent B: | CH$_3$CN/water 90:10 |

| Gradient Table: | Time (minutes) | % Eluent A | % Eluent B |
| --- | --- | --- | --- |
| (linear gradient) | 0 | 60 | 40 |
| | 5 | 60 | 40 |
| | 15 | 0 | 100 |
| | 20 | 0 | 100 |
| | 23 | 60 | 40 |
| | 25 | stop | |

Retention Times:

3-Chloromethylbenzoyl chloride 12.28 min.
3-Chloromethylbenzoic acid (formed by hydrolysis of the acid chloride) 3.46 min.
(3-Chloromethyl)benzoic acid chloromethyl ester 11.67 min.
Methanediol bis [3-chloromethyl)benzoate] (2) 14.67 min.

EXAMPLE 2

Preparation of (2R,3R)-3-[4-(4-cyanophenyl) thiazol-2-yl]-2-(2,4-difluorophenyl)-1-(1H-1,2,4-triazol-1-yl)-2-[[m-(N, N-diethylaminomethyl) benzoyloxy]methoxy]butane

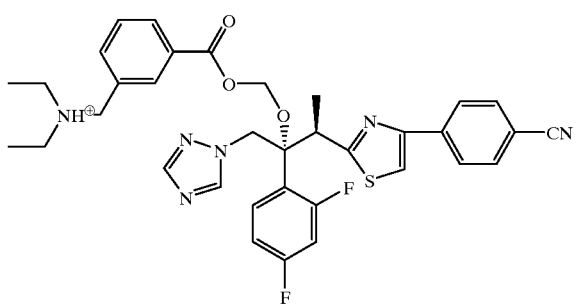

(2R, 3R)-3-[4-(4-cyanophenyl)thiazol-2-yl]-2-(2,4-difluorophenyl)-1-(1H-1,2,4-triazol-1-yl)-2-[[(m-chloromethyl)benzoyloxy]methoxy]butane

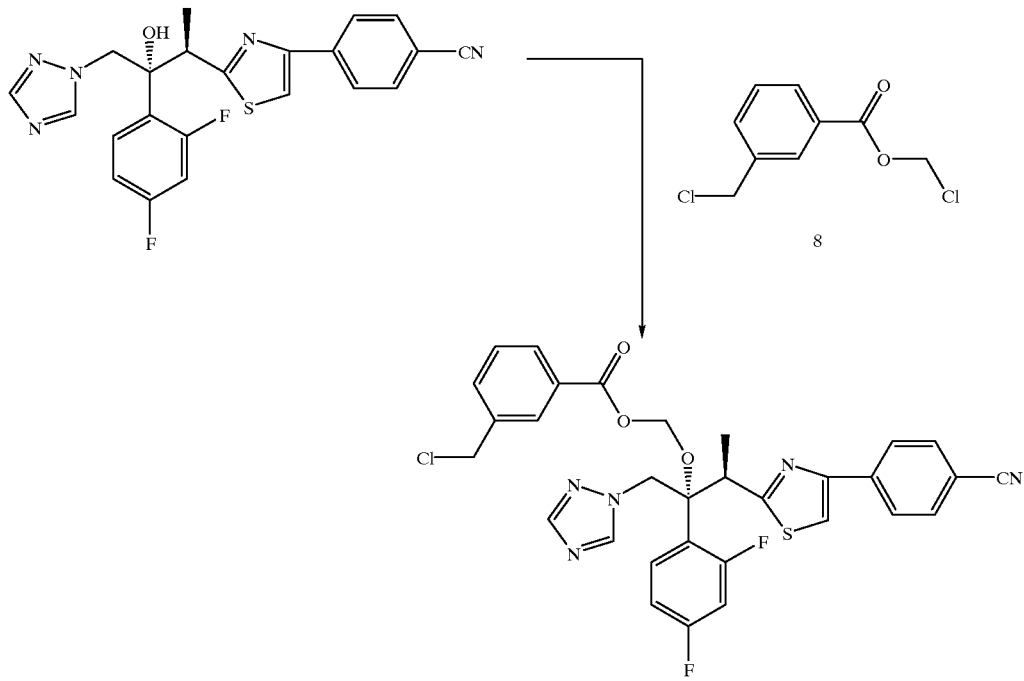

(2R,3R)-3-[4-(4-cyanophenyl)thiazol-2-yl]-2-(2,4-difluorophenyl)-1-(1H-1,2,4-triazol-1-yl)butan-2-ol (1.09 mmol) was added to a suspension of potassium hydride (1.31 mmol) in THF at 0° C. The heterogeneous mixture was stirred for 0.25 hours and chloride 8 (1.14 mmol, prepared via the method of Iyer et al, Syn. Comm. 25, 2739, 1995) was added. The reaction was allowed to stir at 0° C. for 2 hours, and then was allowed to warm to room temperature and stirred for 7 hours. The excess base was carefully quenched with water, and the crude reaction was extracted into ethyl acetate. The layers were separated and the organic layer was washed with water, brine, and was dried over Na$_2$SO$_4$. Purification of the crude product via column chromatography yielded 300 mg of the subtitled compound as a colorless oil. $^1$H NMR (CDCl$_3$) δ 8.11 (s, 1H), 7.94 (d, 2H, J=8.5), 7.88 (s, 1H), 7.79 (d, 1H, J=7.8), 7.70 (m, 3H), 7.56 (d, 1H, J=7.8), 7.42 (m, 2H), 7.29 (m, 1H), 6.85 (m, 2H), 6.20 (s, 2H), 5.35 (d, 2H, J=18), 5.03 (d, 2h, J=18), 4.14 (m, 1H), and 1.29 (m, 3H). MS (M+=619).

(2R,3R)-3-[4-(4-cyanophenyl)thiazol-2-yl]-2-(2,4-difluorophenyl)-1-(1H-1,2,4-triazol-1-yl)-2-[[(m-N-N-diethylaminomethyl)benzoyloxy]methoxy]butane hydrogen chloride

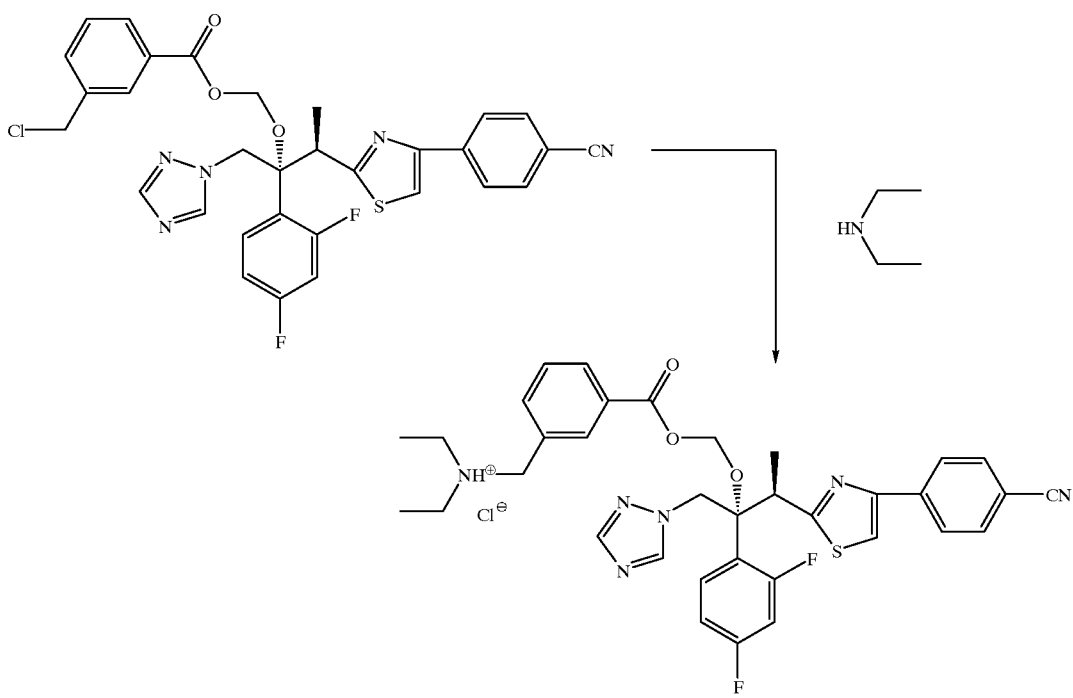

N-N-diethyl amine (1.66 mmol) was added to a solution of (2R,3R)-3-[4-(4-cyanophenyl)thiazol-2-yl]-2-(2,4-difluorophenyl)-1-(1H-1,2,4-triazol-1-yl)-2-[[(m-chloromethyl)benzoyloxy]methoxy]butane (0.33 mmol) in DMF (5 mL). The solution was heated to 40 ° C. for 3 hours, was cooled to room temperature, and the DMF and excess diethyl amine were removed at reduced pressure. Et$_2$O was added (2 mL), followed by 2 mL of a 1M solution of HCl in Et$_2$O, and the resulting solution was allowed to stir at room temperature overnight. The crude reaction was evaporated to dryness, and the resulting light yellow solid was dissolved in H$_2$O (ca 30 mL) and lyophilized, resulting in 223 mg of the subtitled compound as a yellow solid. $^1$H NMR (DMSO) δ 11.06 (br s, 1H), 9.00 (br s, 1H), 8.66 (br s, 1H), 8.23 (s, 1H), 8.06 (m, 2H), 7.96 (m, 2H), 7.87 (d, 2H, J=8), 7.82 (m, 1H), 7.47 (m, 1H), 7.37 (m, 1H), 7.22 (m, 1H), 7.02 (m, 1H), 6.04 (s, 2H), 5.39 (d, 1H, J=16), 5.21d, 1H, J=16), 4.46 (m, 4H), 4.30 (m, 2H), 4.07 (m, 1H), and 1.21 (m, 9H). MS (M+= 619).

What is claimed is:

1. A process for the preparation of a compound of the formula

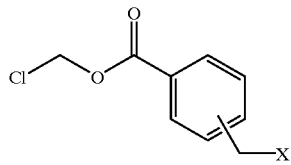

I wherein X is Cl, Br or I and the halomethyl substituent is in the ortho, meta or para position of the phenyl ring, which comprises reacting an acid chloride of the formula

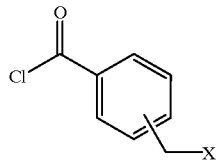

wherein X is Cl, Br or I and the halomethyl substituent is in the ortho, meta or para position of the phenyl ring with SnCl$_4$ and 1,3,5-trioxane in an inert organic solvent.

* * * * *